(12) United States Patent
Clerc

(10) Patent No.: US 9,980,837 B2
(45) Date of Patent: May 29, 2018

(54) DELIVERY DEVICE FOR PARTIALLY UNCONSTRAINED ENDOPROSTHESIS

(71) Applicant: Boston Scientific Scimed, Inc., Maple Grove, MN (US)

(72) Inventor: Claude O. Clerc, Marlborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 28 days.

(21) Appl. No.: 14/210,604

(22) Filed: Mar. 14, 2014

(65) Prior Publication Data

US 2014/0277565 A1 Sep. 18, 2014

Related U.S. Application Data

(60) Provisional application No. 61/798,794, filed on Mar. 15, 2013.

(51) Int. Cl.
*A61F 2/95* (2013.01)
*A61F 2/962* (2013.01)
(Continued)

(52) U.S. Cl.
CPC ................ *A61F 2/95* (2013.01); *A61F 2/962* (2013.01); *A61F 2002/045* (2013.01); *A61F 2002/9505* (2013.01); *A61F 2002/9665* (2013.01)

(58) Field of Classification Search
CPC .... A61F 2/95; A61F 2002/9505; A61F 2/962; A61F 2002/9655
(Continued)

(56) References Cited

U.S. PATENT DOCUMENTS 5,201,757 A  4/1993  Heyn et al.
6,331,186 B1  12/2001  Wang et al.
(Continued)

FOREIGN PATENT DOCUMENTS

CN  103702635 A  4/2014
EP  2529701 A1  12/2012
(Continued)

OTHER PUBLICATIONS

PCT International Search Report, International Application No. PCT/US2014/027871, dated Aug. 4, 2014; 5 pages.
(Continued)

*Primary Examiner* — Thomas J Sweet
*Assistant Examiner* — Daniel Bissing
(74) *Attorney, Agent, or Firm* — Seager, Tufte & Wickhem, LLP

(57) ABSTRACT

An delivery device including an inner tube having an inner tube proximal end region and an inner tube distal end region, the inner tube distal end region comprising a first retaining mechanism; a middle tube having a middle tube distal end region and a middle tube proximal end region and defining a middle tube lumen, the inner tube disposed within the middle tube lumen; and an outer tube having an outer tube proximal end region and an outer tube distal end region and defining an outer tube lumen, the middle tube disposed within the outer tube lumen, the outer tube distal end region comprising a second retaining mechanism; wherein the inner tube is structured and arranged to displace proximally and distally relative to the middle tube, and wherein the outer tube is structured and arranged to displace proximally and distally relative to the middle tube. A method of deploying an endoprosthesis is also disclosed.

16 Claims, 5 Drawing Sheets

(51) Int. Cl.
*A61F 2/966* (2013.01)
*A61F 2/04* (2013.01)

(58) Field of Classification Search
USPC .................................................. 623/1.11, 1.12
See application file for complete search history.

(56) References Cited

U.S. PATENT DOCUMENTS

| | | | |
|---|---|---|---|
| 6,432,130 | B1 | 8/2002 | Hanson |
| 6,562,063 | B1 | 5/2003 | Euteneuer et al. |
| 6,830,575 | B2 | 12/2004 | Stenzel et al. |
| 7,074,236 | B2 | 7/2006 | Rabkin et al. |
| 7,473,271 | B2 * | 1/2009 | Gunderson ............... A61F 2/91 623/1.12 |
| 8,535,368 | B2 * | 9/2013 | Headley, Jr. ............. A61F 2/95 623/1.12 |
| 9,414,915 | B2 * | 8/2016 | Lombardi ............. A61F 2/2418 |
| 2004/0204749 | A1 | 10/2004 | Gunderson |
| 2007/0233222 | A1 * | 10/2007 | Roeder .................... A61F 2/95 623/1.11 |
| 2010/0100167 | A1 * | 4/2010 | Bortlein ................ A61F 2/2436 623/1.11 |
| 2014/0088686 | A1 | 3/2014 | Centola et al. |

FOREIGN PATENT DOCUMENTS

| | | |
|---|---|---|
| WO | 2007098232 A2 | 8/2007 |
| WO | 2010045297 A2 | 4/2010 |

OTHER PUBLICATIONS

PCT Written Opinion of the International Searching Authority, International Application No. PCT/US2014/027871, dated Aug. 4, 2014; 7 pages.

* cited by examiner

DELIVERY DEVICE FOR PARTIALLY UNCONSTRAINED ENDOPROSTHESIS

CROSS REFERENCE TO RELATED APPLICATIONS

This application claims the benefit of provisional U.S. patent application Ser. No. 61/798,794 (entitled ANTI-MIGRATION MICROPATTERNED STENT COATING, filed on Mar. 15, 2013), which is hereby incorporated by reference in its entirety.

The following patent applications are incorporated herein by reference, each in its entirety:

U.S. Pat. App. Ser. No. 61/798,685 (Firstenberg et al.), entitled ANTI-MIGRATION MICROPATTERNED STENT COATING, filed on Mar. 15, 2013;

U.S. Pat. App. Ser. No. 61/798,897 (Seddon et al.), entitled ANTI-MIGRATORY STENT COATING, filed on Mar. 15, 2013;

U.S. Pat. App. Ser. No. 61/799,312 (Fleury et al.), entitled SUPERHYDROPHOBIC COATING FOR AIRWAY MUCUS PLUGGING PREVENTION, filed on Mar. 15, 2013;

U.S. Pat. App. Ser. No. 61/798,545 (Leanna et al.), entitled MEDICAL DEVICES HAVING MICROPATTERN, filed on Mar. 15, 2013; and U.S. Pat. App. Ser. No. 61/798,991 (Bertolino et al.), entitled BIOPSY TOOL HAVING MICROPATTERN, filed on Mar. 15, 2013.

FIELD

This disclosure relates to a delivery device for an endoprosthesis (e.g., an intraluminary prosthesis). Particularly, it relates to a delivery device for placing an endoprosthesis at a desired location within a body lumen (e.g., a gastrointestinal tract of a body).

BACKGROUND

An intraluminary prosthesis (e.g., a stent), is a medical device used in, for example, the treatment of body lumens (e.g., diseased body lumens). A stent is generally a longitudinal tubular structure configured to radially expand when deployed at a desired implant site.

Although endoprosthesis delivery devices are well-known in the art, the assembly of such a delivery device is often complicated. Also, loading an endoprosthesis in such delivery device may be often difficult and time-consuming. For example, an endoprosthesis may be a polymeric or plastic self-expanding stent, which may be difficult to load on a delivery device due to its length. In some cases, elongation of the endoprosthesis may be required while loading in the delivery device. An elongated endoprosthesis may be difficult to accurately deliver at a desired location. For delivery of a relatively long endoprosthesis, a corresponding delivery device may be long or a high delivery force may be required.

Some endoscopic delivery devices are described by Heyn et al. (U.S. Pat. No. 5,201,757), Wang et al. (U.S. Pat. No. 6,331,186), Hanson (U.S. Pat. No. 6,432,130), Euteneuer et al. (U.S. Pat. No. 5,562,063), Stenzel et al. (U.S. Pat. No. 6,830,575), and Rabkin et al. (U.S. Pat. No. 7,074,236).

Thus, there exists a need for improved endoscopic delivery devices suitable for delivering an endoprosthesis, such as a stent. In particular, there exists a need for improved endoscopic delivery devices suitable for delivering an endoprosthesis having a length of about 30 centimeters or greater.

Without limiting the scope of the present disclosure, a brief summary of some of the claimed embodiments is provided below. Additional details of the summarized embodiments and/or additional embodiments can be found in the detailed description.

A brief abstract of the technical disclosure in the specification is provided as well for the purposes of complying with 37 C.F.R. 1.72. The abstract is not intended to be used for interpreting the scope of the claims.

All patents (e.g., U.S. patents) and patent applications (e.g., U.S. patent applications), and all other published documents mentioned anywhere in this application are incorporated herein by reference, each in its entirety.

SUMMARY

In at least one embodiment, the present disclosure is directed to a delivery device (e.g., an endoscopic delivery device) including an inner tube having an inner tube proximal end region and an inner tube distal end region, a middle tube having a middle tube distal end region and a middle tube proximal end region and defining a middle tube lumen, and an outer tube having an outer tube proximal end region and an outer tube distal end region and defining an outer tube lumen. The inner tube is disposed within the middle tube lumen and the middle tube is disposed within the outer tube lumen. The inner tube distal end region includes a first retaining mechanism and the outer tube distal end region includes a second retaining mechanism. In at least one embodiment, the inner tube is structured and arranged to displace proximally and distally relative to the middle tube, and the outer tube is structured and arranged to displace proximally and distally relative to the middle tube.

In at least one embodiment, the present disclosure is directed to a method of deploying an endoprosthesis mounted about a tube including providing an delivery device including a tube on which an endoprosthesis is mounted, a first retaining mechanism extending longitudinally over a first end of the endoprosthesis, and a second retaining mechanism extending longitudinally over a second end of the endoprosthesis. The method further includes longitudinally displacing the first retaining mechanism from the first end of the device; and longitudinally displacing the second retaining mechanism from the second end of the device.

BRIEF DESCRIPTION OF THE FIGURES

The present disclosure, including the following detailed description of certain embodiments, can be understood with reference to the following figures.

DETAILED DESCRIPTION

Figure 1:
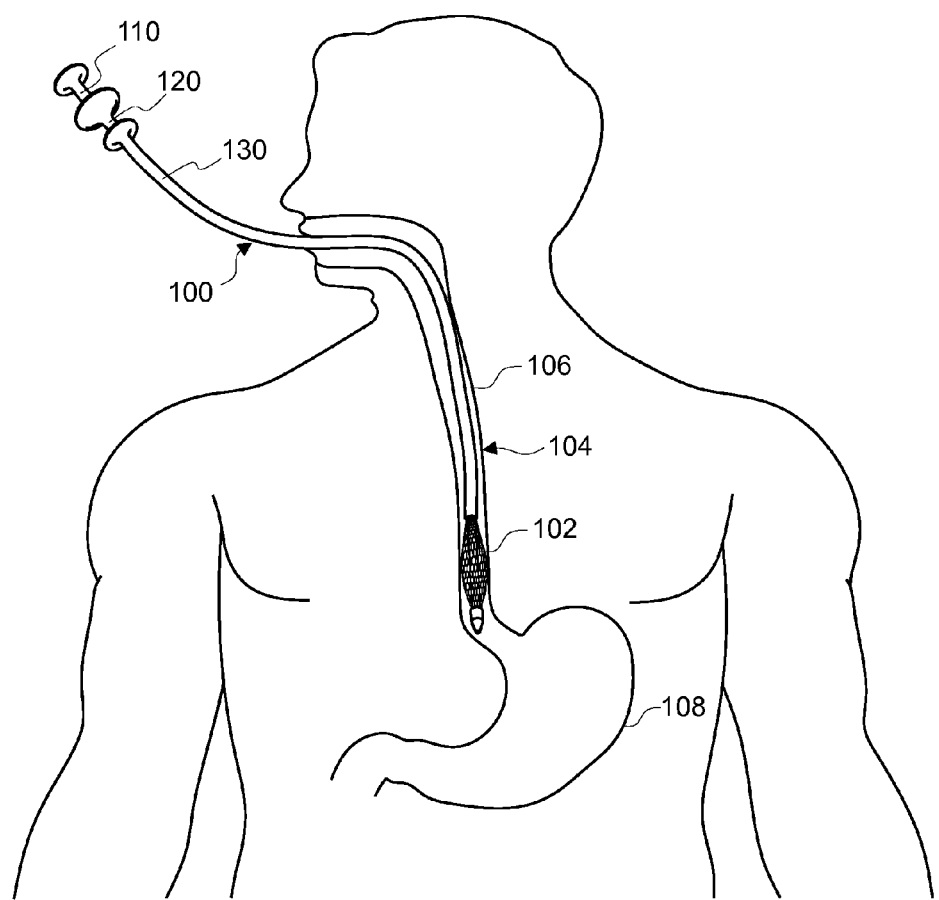
FIG. 1 illustrates a schematic view of a delivery device, in accordance with an exemplary embodiment of the present disclosure, that includes an endoprosthesis to be deployed at a desired location within a lumen of a body.

While the subject matter of the present disclosure can be embodied in many different forms, specific embodiments of the subject matter of the present disclosure are described in detail herein. This description is an exemplification of the principles of the present disclosure and is not intended to limit the present disclosure to the particular embodiments illustrated.

For the purposes of this disclosure, like reference numerals (e.g., in the figures) shall refer to like features unless otherwise indicated. For example, reference numeral 110 in FIG. 1 and reference numeral 110 in FIG. 2 refer to like features (an inner tube). Moreover, inner tube 110, as depicted in a given figure, may include any of the structures or characteristics depicted in another figure or otherwise described herein.

Various aspects of the present disclosure are depicted in the figures. Elements depicted in one figure may be combined with and/or substituted for elements depicted in any other another figure, as may be desired by one of ordinary skill in the art.

The terms "proximal" and "distal" described in relation to various devices, apparatuses, and components—as discussed in the text of the present disclosure—are referred with a point of reference. The point of reference, as used in this description, is a perspective of an operator. The operator can be, for example, a surgeon, a physician, a nurse, a doctor, a technician, or the like, who may perform the procedure of delivery and placement of the disclosed system/device into a patient's body, as described in the present disclosure. The term "proximal" refers to an area or portion that is closer or closest to the operator during a placement procedure. The term "distal" refers to an area or portion that is farther or farthest from the operator during a placement procedure.

FIG. 1 illustrates a schematic view of a delivery device 100 (e.g., an endoscopic delivery device) having an endoprosthesis 102 to be placed at a desired location within a lumen of a body. The lumen of the body can be any suitable lumen, passage, or passageway in the body. For example, an exemplary suitable lumen may be a gastrointestinal tract 104 (e.g., extending from the mouth to the anus) as shown in FIG. 1. FIG. 1 illustrates a portion of the gastrointestinal tract 104 that includes, for example, an esophagus 106 and a stomach 108. In one or more embodiments, the delivery device 100 can be inserted through a mouth for deploying/delivering the endoprosthesis 102 within the gastrointestinal tract 104. In one or more embodiments, the delivery device 100 can be inserted through a nostril for deploying the endoprosthesis 102. Although gastrointestinal tract 104 of FIG. 1 is shown as an exemplary body lumen in which an endoprosthesis 102 may be delivered, it should be noted that an endoprosthesis 102 may be delivered in other body lumens, without limitation.

Figure 2:
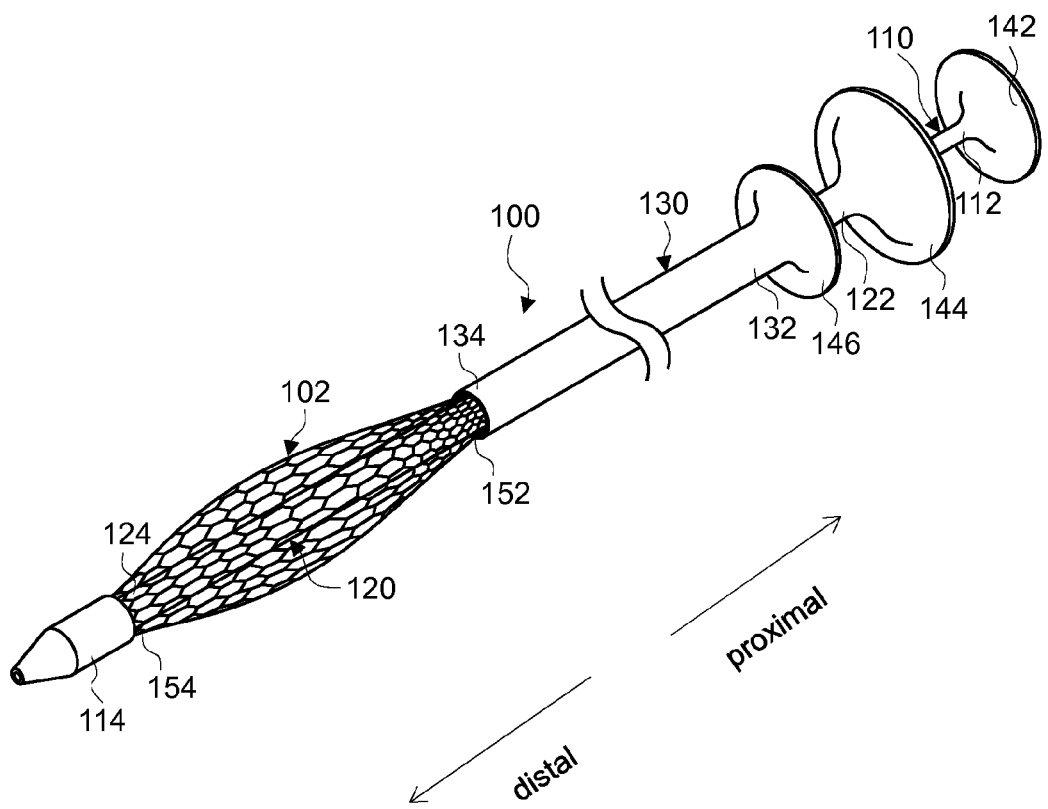
FIG. 2 illustrates an enlarged perspective view of the delivery device, in accordance with an exemplary embodiment of the present disclosure, of FIG. 1 having nested tubes and the endoprosthesis.

As shown in FIGS. 1 and 2, the delivery device 100 includes a plurality of elongate tubes. In at least one embodiment, the delivery device includes, for example, three nested (e.g., concentric) tubes, such as an inner tube 110, a middle tube 120, and an outer tube 130. Other details of inner tube 110, middle tube 120, outer tube 130, and other aspects of delivery device 100 are further described herein.

FIG. 2 illustrates an enlarged perspective view of delivery device 100 (e.g., of FIG. 1) having elongate nested (e.g., concentric) tubes including inner tube 110, middle tube 120, and outer tube 130. In FIG. 2, the inner tube 110 may include an inner tube proximal end region 112 and an inner tube distal end region 114 that may include a first retaining mechanism 160 (see FIG. 3A). The middle tube 120 may include a middle tube proximal end region 122 and a middle tube distal end region 124. Middle tube 120 may define a middle tube lumen (e.g., extending from the middle tube proximal end region 122 to the middle tube distal end region 124). The inner tube 110 may be disposed within the middle tube lumen.

The inner tube distal end region 114 may be distal of the middle tube distal end region 124. The inner tube 110 may be structured and arranged to displace (e.g., translate, slide, move, etc.) proximally and distally relative to (e.g., within, etc.) the middle tube 120. The outer tube 130 includes an outer tube proximal end region 132 and an outer tube distal end region 134. The outer tube 130 defines an outer tube lumen (e.g., extending from the outer tube proximal end region 132 to the outer tube distal end region 134). The middle tube 120 is disposed within the outer tube lumen.

Figure 3A:
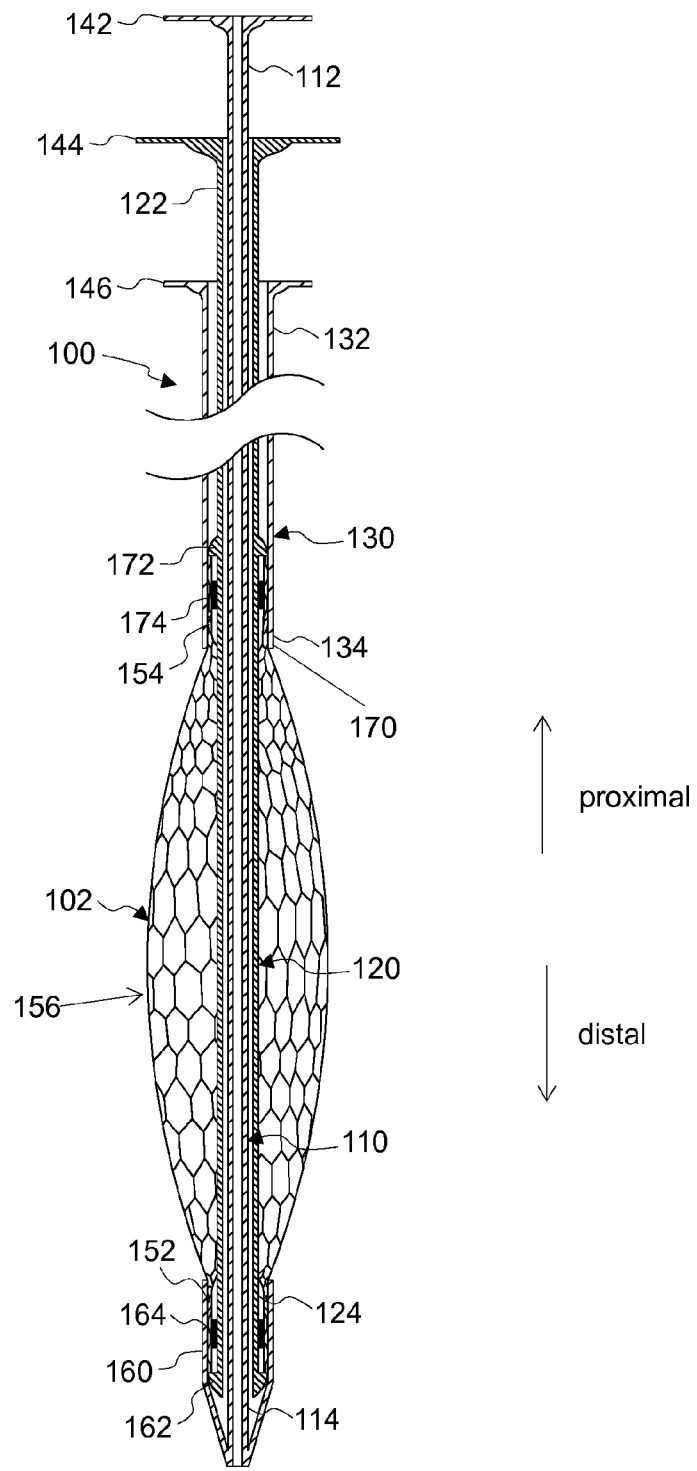
FIG. 3A illustrates a cross-sectional view of the delivery device, in accordance with an exemplary embodiment of the present disclosure, with proximal and distal ends of the endoprosthesis secured while a medial portion of the endoprosthesis is unconstrained.
Figure 3B:
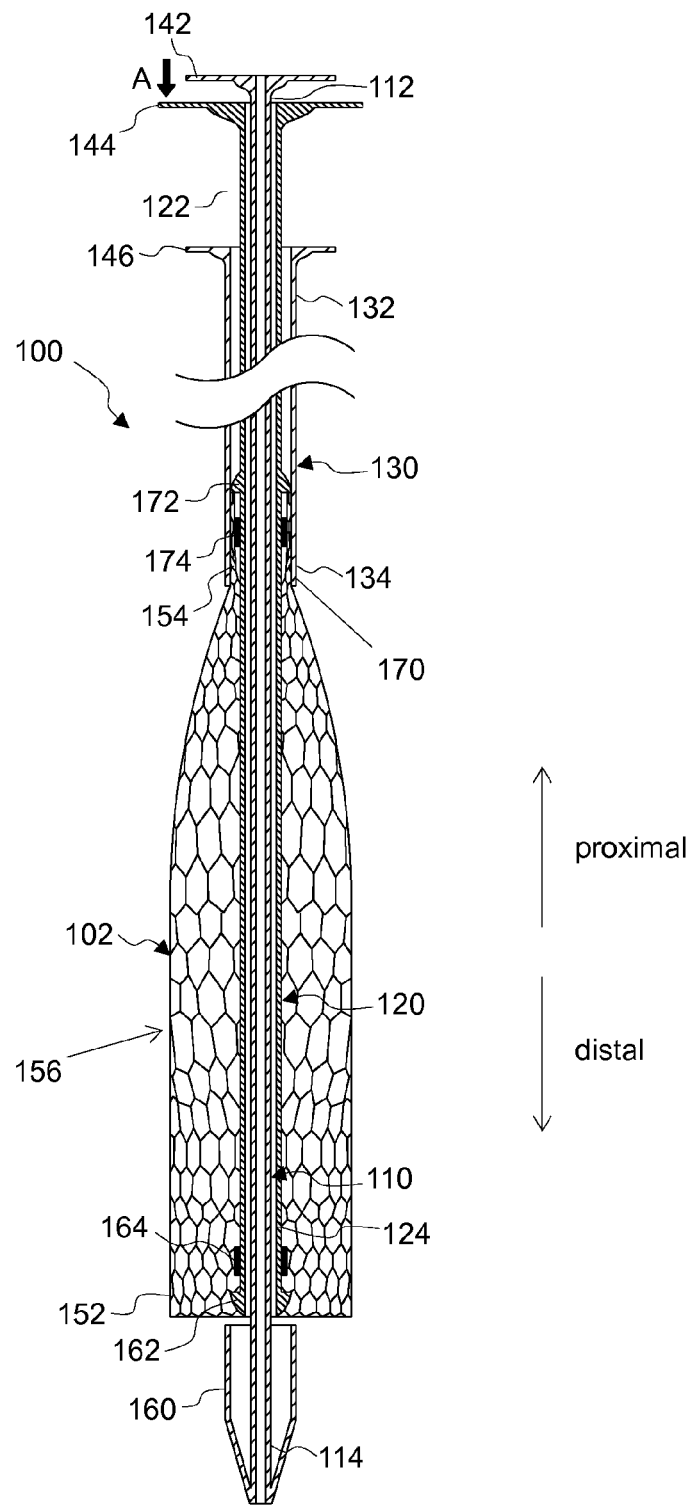
FIG. 3B illustrates a cross-sectional view of the delivery device, in accordance with an exemplary embodiment of the present disclosure, with an unconstrained distal end of the endoprosthesis and medial portion of the endoprosthesis.
Figure 3C:
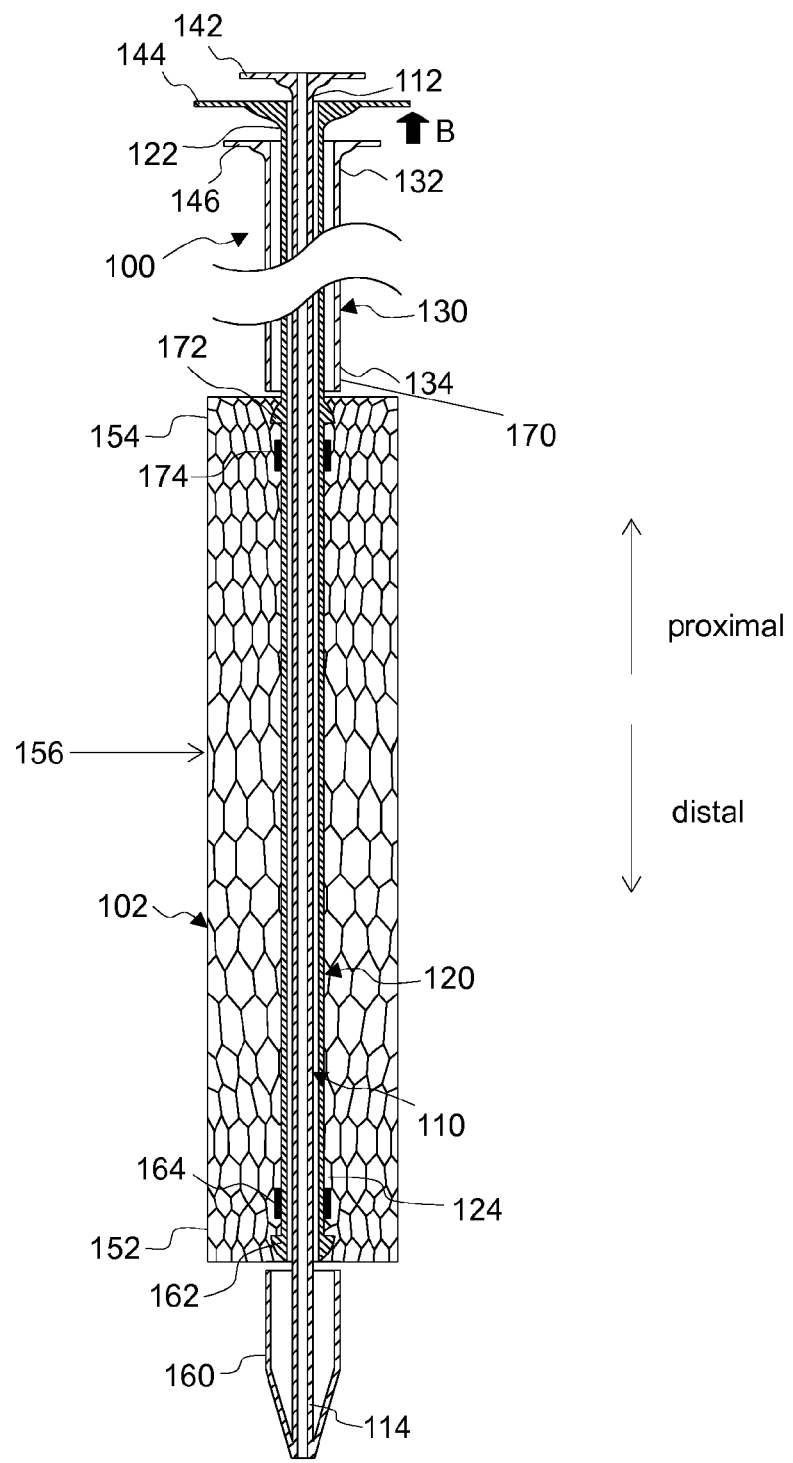
FIG. 3C illustrates a cross-sectional view of the delivery device, in accordance with an exemplary embodiment of the present disclosure, with unconstrained distal and proximal ends of the endoprosthesis and medial portion of the endoprosthesis.

In at least one embodiment, as shown in FIGS. 3A-3C, the outer tube 130 is concentric about the middle tube 120 and/or the middle tube 120 is concentric about the inner tube 110. That is, the inner tube 110 may have the same centerline (e.g., longitudinal axis) as the middle tube 120 and/or outer tube 130, and vice versa. As shown in FIG. 3A, the distal end region 124 of the middle tube 120 is distal of the distal end region 134 of the outer tube 130. The outer tube 130 may be structured and arranged to displace proximally and distally relative to (e.g., over, etc.) the middle tube 120.

Endoscopic delivery device 100 may be used to deliver endoprosthesis 102, as shown in FIG. 2.

Each of the inner tube 110, middle tube 120, and outer tube 130 may include (e.g., be made of, be formed from, etc.) a flexible biocompatible plastic material and may be manufactured using any of a wide variety of suitable manufacturing methods including, but not limited to, extrusion.

In one or more embodiments, the delivery device 100 may further include a first handle 142 attached to (e.g., operatively engaged to, extending from, incorporated with, adhered to, bonded to, friction fitted to, etc.) the proximal end region 112 of the inner tube 110. Similarly, the delivery device 100 may include a second handle 144 and a third handle 146 attached to the middle tube proximal end region 122 and the outer tube proximal end region 132, respectively. In at least one embodiment shown in FIG. 3A, the second handle 144 may be distal of the first handle 142 and the third handle 146 can be distal of the second handle 144. In some embodiments, there may be a first distance (e.g., in the longitudinal direction parallel to the longitudinal axis of the inner tube 110) between the first handle 142 and the second handle 144, which may be in a range of about 0 centimeters to about 2 centimeters (e.g., about 1 to about 2 centimeters). The present disclosure also contemplates a first distance greater than 2 centimeters. Similarly, there may be a second distance between the second handle 144 and the third handle 146, which may be in a range of about 0 centimeters to 2 centimeters (e.g., about 1 to about 2 centimeters). The present disclosure also contemplates a second distance up to greater than 2 centimeters (e.g., up to 3 centimeters, up to 5 centimeters, up to 10 centimeters, etc.). Each of the first handle 142, second handle 144, and third handle 146 may be made of a rigid material that may include, but is not limited to, one or more plastics, one or more metals, or a combination of these. In some embodiments, the first handle 142, second handle 144, and third handle 146 may be integrally molded or extruded with the inner tube proximal end region 112, middle tube proximal end region 122, and the outer tube proximal end region 132, respectively.

As shown in, for example, FIG. 3A, an endoprosthesis 102 may be deployed about (e.g., concentric about) and on the middle tube 120 in preparation of and/or during delivery/deployment of the endoprosthesis 102. That is, endoprosthesis 102 may define an endoprosthesis lumen extending longitudinally from an endoprosthesis proximal end 152 to an endoprosthesis distal end 154, wherein at least a portion of middle tube 120 is disposed within the endoprosthesis lumen. Specifically, the endoprosthesis 102 may include an endoprosthesis proximal end 152 and an endoprosthesis distal end 154, none, one, or both of which may be constrained on (e.g., biased against, attached to, etc.) the middle tube 120. For example, in FIG. 3A, both of the endoprosthesis proximal end 152 and the endoprosthesis distal end 154 are constrained on the middle tube 120. In at least one embodiment, the inner tube distal end region 114 can include a first retaining mechanism 160 adapted to constrain the endoprosthesis distal end 152 on the middle tube 120, and the outer tube distal end region 134 can include a second retaining mechanism 170 adapted to constrain the endoprosthesis proximal end 154 on the middle tube 120. The first retaining mechanism 160 and second retaining mechanism 170 are explained later in greater detail herein, for example, in conjunction with FIG. 3A. The endoprosthesis 102 can further include an unconstrained medial region 156 between the endoprosthesis proximal end 152 and the endoprosthesis distal end 154. The unconstrained medial region 156 may extend farther from the middle tube 120 (e.g., in a radial direction) than the constrained endoprosthesis proximal end 152 and/or the endoprosthesis distal end 154.

An endoprosthesis delivered by the endoprosthesis delivery system 100 of the present disclosure may have any of a wide variety of endoprosthesis architectures or designs without limitation. As shown in FIG. 3A, the endoprosthesis 102 may include, for example, a portion having a mesh construction formed from at least one wire made from a metal, alloy, plastic, composite, or any other suitable material such as Nitinol. The wire may be knitted, woven, or braided into a plurality of overlapping loops to form a wire mesh portion. The endoprosthesis may also be manufactured from a laser cut nitinol tube. In some embodiments, one or both of the endoprosthesis proximal end 152 and the endoprosthesis distal end 154 may be flared (i.e., the diameter of one or both terminal ends, when unconstrained, may be greater than the diameter of the unconstrained medial portion). Further, the endoprosthesis 102 may optionally include a membrane extending around at least a portion between the endoprosthesis proximal end 152 and endoprosthesis distal end 154. The membrane can be made from any of a wide variety of suitable materials such as expanded polytetrafluoroethylene (ePTFE), latex, silicone, etc. In one or more embodiments, the endoprosthesis 102 may include a cover or liner on the inside and/or outside of the endoprosthesis to facilitate sliding the endoprosthesis through a body lumen during delivery. The cover or liner may be formed from silicone or urethane for example or ePTFE. Such a cover or liner may include a lubricious outer surface to facilitate endoprosthesis delivery.

In some embodiments, the endoprosthesis 102 can be a prosthesis having a length of greater than about 12 centimeters (e.g., greater than 24 centimeters, greater than 30 centimeters, greater than 45 centimeters, in a range of from about 30 centimeters to about 60 centimeters, etc.). In some embodiments, the endoprosthesis 102 may be a self-expanding prosthesis adapted to radially expand (e.g., extend, etc.) upon removal of a force from one or both of the constrained endoprosthesis proximal end 152 and endoprosthesis distal end 154. Also, in at least one embodiment, the endoprosthesis 102 can be configured to exert a low radial force. The low radial force may facilitate mitigating undesirable physiological responses, such as lumen wall inflammation and thrombosis formation, and permitting the endoprosthesis 102 to move flexibly in response to external forces such as due to changes in the dimensions of the body lumen or due to posture changes.

FIG. 3A illustrates a cross-sectional view of the delivery device 100 with the endoprosthesis proximal end 152 and endoprosthesis distal end 154 of the endoprosthesis 102 held in place (e.g., secured) on the middle tube 120 by the second retaining mechanism 170 and the first retaining mechanism 160, respectively. In some embodiments, the first retaining mechanism 160 can be a sleeve provided on the inner tube distal end region 114. For example, the first retaining mechanism 160 may be a substantially hollow frusto-conical structure that extends proximally from the inner tube distal end region 114 (e.g., from the inner tube terminal distal end). In one or more embodiments, the first retaining mechanism 160 may be a separate hollow sleeve component coupled to the inner tube distal end region 114. As shown in FIG. 3A, the first retaining mechanism 160 may define a cavity within which the endoprosthesis distal end 152 may be received. In at least one embodiment, the first retaining mechanism extends in a longitudinal direction proximally over the endoprosthesis distal end 152. In some embodiments, the first retaining mechanism 160 can extend approximately 1 to 2 centimeters over the endoprosthesis distal end 154. That is, the prosthesis distal end 152 may be disposed up to about 2 centimeters into a cavity defined by the first retaining mechanism 160. The present disclosure also contemplates first retaining mechanisms having a cavity that extends longer than 2 centimeters in the longitudinal direction and may be configured and arranged to overlap the endoprosthesis distal end 152 by more than 2 centimeters or, alternatively, about 2 centimeters or less. In one or more embodiments, the longitudinal length of the overlap of the first retaining mechanism 160 over the endoprosthesis distal end 152 may be less than the distance that the first handle may move relative to (e.g., toward) the second handle. For example, if the first handle 142 may move up to about 2 centimeters toward the second handle 144, then the extent of overlap of the first retaining mechanism 160 over the endoprosthesis distal end 152 may be less than or equal to about 2 centimeters. When the first handle 142 is moved closer toward the second handle 144, the extent of overlap of the first retaining mechanism 160 over the endoprosthesis distal end 152 is reduced until the first retaining mechanism 160 does not overlap the endoprosthesis distal end 152 (e.g., FIG. 3B), thereby releasing the endoprosthesis distal end 152 from the first retaining mechanism 160 and allowing the endoprosthesis distal end 152 to radially expand.

In one or more embodiments, the delivery device 100 may include a distal stopper 162 and a distal endoprosthesis holder 164 on the middle tube distal end region 124. The distal stopper 162 and distal endoprosthesis holder 164 along with the sleeve of the first retaining mechanism 160 may be adapted to hold the endoprosthesis proximal end 152 of the endoprosthesis 102 in place, i.e., about the middle tube distal end region 124. The distal stopper 162 may be a raised portion (e.g., an annular ridge) configured at an extreme end (e.g., terminal end) of the middle tube distal end region 124. In at least one embodiment, the distal stopper 162 may be an integral portion of the middle tube distal end region 124. In at least one embodiment, the distal stopper 162 may be a separate component attached to the middle tube 120 and may take the form of a ring, coupled to the middle tube distal end region 124. The distal stopper 162 may be configured to restrict or constrain axial movement of the endoprosthesis distal end 152 of the endoprosthesis 102 in the distal direction when the endoprosthesis 102 is placed (e.g., concentrically placed) about the middle tube 120.

In one or more embodiments, the distal endoprosthesis holder 164 is configured proximal of, but near, the distal stopper 162, on the middle tube distal end region 124. The distal endoprosthesis holder 164 may be defined as a raised portion. In various embodiments, the distal endoprosthesis holder 164 can be an integral portion of, or a separate component coupled to, the middle tube distal end region 124. In some embodiments, the distal stopper 162 may extend radially from the middle tube 120 a greater distance than the distal endoprosthesis holder 164 extends radially from the middle tube 120. Further, a difference between the thicknesses (e.g., radial dimension) of the distal stopper 162 and the distal endoprosthesis holder 164 may be less than or equal to a thickness of the endoprosthesis distal end 152 of the endoprosthesis 102. This may allow accommodation of the endoprosthesis distal end 152 of the endoprosthesis 102 between the sleeve of the first retaining mechanism 160 and the distal endoprosthesis holder 164 for securing the endoprosthesis distal end 152 in place on the middle tube 120. In one or more embodiments securing an endoprosthesis (or a portion thereof) to a tube (e.g., a middle tube 120, etc.) is meant to include securing an endoprosthesis (or a portion thereof) to an endoprosthesis holder (e.g., distal endoprosthesis holder 164, proximal endoprosthesis holder 174, etc.) engaged with or incorporated into the tube (e.g., middle tube 120, etc.).

As mentioned above, the second retaining mechanism 170 may be adapted to hold the endoprosthesis proximal end 154 in place on the middle tube 120. In some embodiments, the second retaining mechanism may include and/or take the form of a sleeve. In the one or more embodiments of FIGS. 3A-3C, the second retaining mechanism 170 may be defined by the distal end region 134 of the outer tube 130. Specifically, the distal end region 134 of the outer tube 130 defines a sleeve that may act as the second retaining mechanism, as shown in FIG. 3A. In one or more embodiments, the second retaining mechanism 170 may include a separate hollow sleeve-type structure, such as a cylindrical or a conical sleeve, which may be coupled to or integral with the distal end region 134 of the outer tube 130. The second retaining mechanism 170 may be configured to extend distally over the endoprosthesis proximal end 154 for holding the endoprosthesis proximal end 154 in place. In some embodiments, the second retaining mechanism 170 may extend in a longitudinal direction approximately 0 to 2 centimeters over the endoprosthesis proximal end 154. That is, the prosthesis proximal end 154 may be disposed up to about 2 centimeters into a cavity defined by the second retaining mechanism 170. The present disclosure also contemplates second retaining mechanisms having a cavity that extends longer than 2 centimeters in the longitudinal direction and may be configured and arranged to overlap the endoprosthesis proximal end 154 by more than 2 centimeters or, alternatively, about 2 centimeters or less. In one or more embodiments, the longitudinal length of the overlap of the second retaining mechanism 170 over the endoprosthesis proximal end 154 may be less than the distance that the third handle 146 may move relative to (e.g., toward) the second handle 144. For example, if the third handle 146 may move up to about 2 centimeters toward the second handle 144, then the extent of overlap of the second retaining mechanism 170 over the endoprosthesis proximal end 154 may be less than or equal to about 2 centimeters. When the third handle 146 is moved closer toward the second handle 144, the extent of overlap of the second retaining mechanism 170 over the endoprosthesis proximal end 154 is reduced until the second retaining mechanism 170 does not overlap the endoprosthesis proximal end 154 (e.g., FIG. 3C), thereby releasing the endoprosthesis proximal end 154 from the second retaining mechanism 170 and allowing the endoprosthesis proximal end 154 to radially expand.

In one or more embodiments, a first retaining mechanism may be structured and arranged in any manner such that the endoprosthesis distal end is secured. For example, a first retaining mechanism may utilize a crochet suture rather than the sleeve shown in FIGS. 3A-3C to retain the endoprosthesis distal end 152. Similarly, second retaining mechanism 170 may utilized a crochet suture to secure the endoprosthesis proximal end 154 rather than overlapping the endoprosthesis proximal end 154 with a portion of outer tube 130.

In one or more embodiments, the delivery device 100 may further include a proximal stopper 172 and/or a proximal endoprosthesis holder 174 on the middle tube 120 for securing the endoprosthesis proximal end 154 in place (e.g., within the distal end region 134 of the outer tube 130). In one or more embodiments, the proximal stopper 172 may be a raised portion on the middle tube distal end region 124 and may be located proximal of the distal stopper 162. The proximal stopper 172 may be adapted to restrict axial movement (e.g., in the proximal direction) of the endoprosthesis proximal end 152 of the endoprosthesis 102 away from the distal end region 134 when the endoprosthesis 102 is concentrically placed about the middle tube 120. The proximal endoprosthesis holder 174 may be defined as a raised portion on the middle tube distal end region 124 and may be located proximal of the distal endoprosthesis holder 164. In some embodiments, the proximal stopper 172 may extend radially from the middle tube 120 a greater distance than the proximal endoprosthesis holder 174 extends radially from the middle tube 120. Further, a difference between the thicknesses (e.g., radial dimension) of the proximal stopper 172 and the proximal endoprosthesis holder 174 may be less than or equal to a thickness of the endoprosthesis proximal end 154 of the endoprosthesis 102. This may allow accommodation of the endoprosthesis proximal end 154 of the endoprosthesis 102 between the distal end region 134 of the outer tube 130 and the proximal endoprosthesis holder 174 for securing the endoprosthesis proximal end 152 in place on the middle tube 120.

Specifically, during operation, when the endoprosthesis 102 is placed at (e.g., delivered to) a desired location in a body lumen, for example, at a desired location in the gastrointestinal tract 104 (as shown in FIG. 1), the endoprosthesis 102 may be deployed at the desired location by releasing or freeing the endoprosthesis proximal end 152 and endoprosthesis distal end 154. FIG. 3B illustrates a cross-sectional view of the delivery device 100 with a freed endoprosthesis distal end 152. FIG. 3C illustrates a cross-sectional view of the delivery device 100 with a freed endoprosthesis distal end 152 and endoprosthesis proximal end 154. As shown in FIG. 3B, the endoprosthesis distal end 152 of the endoprosthesis 102 can be unconstrained/freed/released by maneuvering the inner tube 110 and/or first handle 142. Specifically, the first handle 142 may be moved forward (shown with arrow A) with respect to the second handle 144 (e.g., keeping the second handle 144 stationary) for proximally displacing the inner tube 110 within the middle tube 120. For example, a short stroke of about 1 to 2 cm, e.g., the forward (e.g., distal) movement of the first handle 142 with respect to the second handle 144 may be performed. This can cause the sleeve of the first retaining mechanism 160 to move in a distally axial direction (away from the endoprosthesis distal end 152) and thereby release the endoprosthesis distal end 152 from the distal endoprosthesis holder 164. Once the endoprosthesis distal end 152 is released, the endoprosthesis distal end 154 may expand due to, for example, a self-expanding nature of the endoprosthesis 102. In one or more embodiments, the unconstrained endoprosthesis distal end 152 may expand to have a diameter that is greater than the constrained diameter and may be less than, equal to, or greater than the diameter of the unconstrained medial region 156 of the endoprosthesis 102.

In one or more embodiments, as shown in FIG. 3C, the endoprosthesis proximal end 154 of the endoprosthesis 102 may thereafter be unconstrained/freed by maneuvering the outer tube 130 and/or third handle 146. Specifically, the third handle 146 may be moved backward (shown with arrow B) (e.g., in a proximal direction) with respect to the second handle 144 (e.g., keeping the second handle 144 stationary) for proximally displacing the outer tube 130 along the middle tube 120. For example, a short stroke of about 1 to 2 cm, e.g., a backward (proximal) movement of the third handle 146 with respect to the second handle 144 may be performed. This can cause the outer tube distal end region 134 to move in a proximally axial direction (away from the endoprosthesis proximal end 154) and thereby release the endoprosthesis proximal end 154 from the proximal endoprosthesis holder 174. Once the endoprosthesis proximal end 154 is released, the endoprosthesis proximal end 154 may expand due to, for example, a self-expanding nature of the endoprosthesis 102. In one or more embodiments, the unconstrained endoprosthesis proximal end 154 may expand to have a diameter that is greater than the constrained diameter and may be less than, equal to, or greater than the diameter of the unconstrained medial region 156 of the endoprosthesis 102.

Although FIGS. 3B and 3C depict first releasing the endoprosthesis distal end 152 and subsequently releasing the endoprosthesis proximal end 154, the present disclosure contemplates releasing the ends in a different order (proximal end, then distal end) or simultaneously.

Once both of the endoprosthesis proximal end 152 and endoprosthesis distal end 154 are released, the endoprosthesis 102 may expand and may be secured to the desired location in the gastrointestinal tract 104 (or any other bodily lumen the device is intended for delivery in) due to the radial force exerted by the endoprosthesis 102 on the desired location (e.g., the body lumen wall). Thereafter, the inner tube 110, middle tube 120, and outer tube 130 may be removed from the gastrointestinal tract 104 (or other body lumen), which may complete the deployment of the endoprosthesis 102 at the desired location in the gastrointestinal tract 104. For example, the inner tube 110, middle tube 120, and outer tubes 130 may be simply pulled individually or collectively through the gastrointestinal tract 104. In one or more embodiments, the deployed and expanded endoprosthesis 102 may allow an unobstructed passage of, for example, the first retaining mechanism and the middle tube distal end region to be withdrawn (e.g., in a proximal direction) through the expanded endoprosthesis.

The delivery device 100 of the present disclosure may facilitate deploying an endoprosthesis by holding only proximal and distal ends of the endoprosthesis, and by having an unconstrained medial region of the endoprosthesis between the constrained proximal and distal ends. A delivery device of the present disclosure may allow an endoprosthesis to be installed therein at the fully deployed endoprosthesis length, which may be useful for increasing accuracy of placement of the endoprosthesis at a desired location. The delivery device 100 may be capable of delivering and deploying an endoprosthesis having a length of about 30 centimeters to about 60 centimeters or longer. In one or more embodiments, the delivery device 100 may be used to deploy an endoprosthesis for treatment of bariatric leaks, especially after a sleeve gastrectomy (e.g., a surgical weight loss procedure in which a stomach is reduced in size) where an endoprosthesis having a length of about 30 centimeters to about 40 centimeters may be deployed. In one or more embodiments, the delivery device 100 may be used to deploy a metabolic endoprosthesis that may be up to about 60 centimeters in length or longer. In at least one embodiment, the delivery device 100 may also deploy an endoprosthesis having a low radial force, which may easily pass through a body lumen when the medial region of the endoprosthesis is unconstrained. The delivery device 100 may be used to deliver a sticky endoprosthesis in some embodiments, because there may be no membrane on such an endoprosthesis and may require a low delivery force. The delivery device 100 may be capable of delivering endoprosthesis with one or more micropatterns (e.g., micropatterned surfaces, micropatterned polymer coatings, etc.).

In one or more aspects of the present disclosure, a method of deploying an endoprosthesis mounted about a tubular body is provided. For example, in one or more embodiments, a method may include providing a delivery device as described herein. In at least one embodiment, an delivery device includes a tube (e.g., a middle tube 120 as in FIG. 3A) on which an endoprosthesis 102 is mounted, a first retaining mechanism 160 extending longitudinally over a first end (e.g., endoprosthesis distal end 152) of the endoprosthesis 102, and a second retaining mechanism 170 extending longitudinally over a second end (e.g., endoprosthesis proximal end) of the endoprosthesis 102. The method also includes longitudinally displacing the first retaining mechanism from the first end of the endoprosthesis and longitudinally displacing the second retaining mechanism from the second end of the endoprosthesis. In one or more embodiments, the method includes expanding the first end (e.g., endoprosthesis distal end 152) of the endoprosthesis 102 (e.g., after displacing the first retaining mechanism 160).

In one or more embodiments, a first retaining mechanism may be longitudinally displaced by moving the first retaining mechanism away from the first end of the endoprosthesis. In another embodiment, the first retaining mechanism may be longitudinally displaced by moving the first end of the endoprosthesis away from the first retaining mechanism. As described herein, the first retaining mechanism 160 may be or may include a sleeve of the inner tube 110 adapted to constrain the endoprosthesis distal end 152 on or about the middle tube 120. In some embodiments, the first retaining mechanism 160 may be longitudinally displaced by moving the first retaining mechanism 160 away from the distal end region 124 of the middle tube 120. In some embodiments, the first retaining mechanism 160 may be longitudinally displaced by moving the distal end region 124 of the middle tube 120 away from the sleeve 160. The constrained endoprosthesis distal end 152 may accordingly be released when the first retaining mechanism 160 is moved away from the endoprosthesis distal end 152, as shown in FIG. 3B.

In one or more embodiments of the present disclosure, a method may include positioning an unconstrained medial region of an endoprosthesis at a desired location within a lumen of a body (e.g., for deployment of the endoprosthesis at that location). For example, the endoprosthesis 102 may be positioned at a desired location in the gastrointestinal tract 104 by releasing the endoprosthesis proximal end 154 and the endoprosthesis distal end 152, and the unconstrained medial region 156 of the endoprosthesis 102 can expand and contact (e.g., be secured to, etc.) a desired location in the gastrointestinal tract 104. The medial region of the endoprosthesis 102 may be disposed between the endoprosthesis distal end 152 and the endoprosthesis proximal end 154. When the medial region is unconstrained, it may extend from the tube (e.g., a middle tube 120) in a radial direction farther than the one or more constrained endoprosthesis ends.

A description of some exemplary embodiments of the present disclosure is contained in the following numbered statements:

1. A delivery device comprising:
   an inner tube having an inner tube proximal end region and an inner tube distal end region, the inner tube distal end region comprising a first retaining mechanism;
   a middle tube having a middle tube distal end region and a middle tube proximal end region and defining a middle tube lumen, the inner tube disposed within the middle tube lumen; and
   an outer tube having an outer tube proximal end region and an outer tube distal end region and defining an outer tube lumen, the middle tube disposed within the outer tube lumen, the outer tube distal end region comprising a second retaining mechanism;
   wherein the inner tube is structured and arranged to displace proximally and distally relative to the middle tube, and
   wherein the outer tube is structured and arranged to displace proximally and distally relative to the middle tube.
2. The delivery device of statement 1 further comprising a distal stopper on the middle tube in the middle tube distal end region and a proximal stopper on the middle tube, the proximal stopper located proximal of the distal stopper.
3. The delivery device of statement 1 or 2 further comprising a distal endoprosthesis holder on the middle tube in the middle tube distal end region and a proximal endoprosthesis holder on the middle tube, the proximal endoprosthesis holder located proximal of the distal endoprosthesis holder.
4. The delivery device of any of statements 1-3 wherein the distal end region of the inner tube is distal of the distal end region of the middle tube, and wherein the distal end region of the middle tube is distal of the distal end region of the outer tube.
5. The delivery device of any of statements 1-4 further comprising a first handle attached to the proximal end region of the inner tube; a second handle attached to the proximal end region of the middle tube, the second handle distal of the first handle; and a third handle attached to the proximal end region of the outer tube, the third handle distal of the second handle.
6. The delivery device of statement 5 wherein a first distance between the first handle and the second handle is in a range of about 0 centimeters to about 2 centimeters.
7. The delivery device of statement 5 or 6 wherein a second distance between the second handle and the third handle is in a range of about 0 centimeters to about 2 centimeters.
8. The delivery device of any of statements 1-7 further comprising an endoprosthesis that comprises an endoprosthesis distal end constrained on the middle tube by the first retaining mechanism and an endoprosthesis proximal end constrained on the middle tube by the second retaining mechanism, wherein the endoprosthesis defines an endoprosthesis lumen, the middle tube disposed within the endoprosthesis lumen.
9. The delivery device of statement 8 wherein the first retaining mechanism comprises a first sleeve extending proximally over the endoprosthesis distal end.
10. The delivery device of statement 9 wherein the first retaining mechanism extends over the endoprosthesis distal end for a third longitudinal distance in a range of about 0 centimeters to about 2 centimeters.
11. The delivery device of statement 8 wherein the second retaining mechanism comprises a second sleeve extending distally over the endoprosthesis proximal end.
12. The delivery device of statement 11 wherein the second retaining mechanism extends over the endoprosthesis proximal end for a fourth longitudinal distance in a range of about 0 centimeters to about 2 centimeters.
13. The delivery device of statement 8 wherein the endoprosthesis further comprises an unconstrained medial region extending farther from the middle tube than the constrained endoprosthesis distal end and the constrained endoprosthesis proximal end.
14. The delivery device of any of statements 8-13 wherein the endoprosthesis has an endoprosthesis length in a range of about 30 centimeters to about 60 centimeters.
15. The delivery device of any of statements 8-14 wherein the endoprosthesis has a low radial force.
16. A method of deploying an endoprosthesis mounted about a tubular body comprising:
    providing a delivery device comprising a tube on which an endoprosthesis is mounted, a first retaining mechanism extending longitudinally over a first end of the endoprosthesis, and a second retaining mechanism extending longitudinally over a second end of the endoprosthesis;
    longitudinally displacing the first retaining mechanism from the first end of the endoprosthesis; and
    longitudinally displacing the second retaining mechanism from the second end of the endoprosthesis.
17. The method of statement 16 further comprising expanding the first end of the endoprosthesis subsequent to displacing the first retaining mechanism.
18. The method of statement 16 or 17 wherein the first retaining mechanism is longitudinally displaced by moving the first retaining mechanism away from the first end of the endoprosthesis.
19. The method of any of statements 16-18 further comprising positioning an unconstrained medial region of the device at a desired location within a lumen of a body.
20. The method of any of statements 16-19 wherein longitudinally displacing the first retaining mechanism from the first end of the device comprises reducing a first distance between a first handle connected to the first retaining mechanism and a second handle connected to the tube.
21. The method of any of statements 16-20 wherein longitudinally displacing the second retaining mechanism from the second end of the device comprises reducing a second distance between a third handle connected to the second retaining mechanism and a second handle connected to the tube.

22. A device comprising:
an inner member having an inner member proximal end portion and an inner member distal end portion, the inner member distal end portion comprising a first retainer;
a middle member having a middle member distal end portion and a middle member proximal end portion and defining a middle member lumen, the inner member disposed within the middle member lumen; and
an outer member having an outer member proximal end portion and an outer member distal end portion and defining an outer member lumen, the middle member disposed within the outer member lumen, the outer member distal end portion comprising a second retainer;
wherein the inner member is adapted to slide proximally and distally relative to the middle member, and
wherein the outer member is adapted to slide proximally and distally relative to the middle member.

The present disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to."

Further, the particular features presented in the dependent claims can be combined with each other in other manners within the scope of the present disclosure such that the present disclosure should be recognized as also specifically directed to other embodiments having any other possible combination of the features of the dependent claims. For instance, for purposes of claim publication, any dependent claim which follows should be taken as alternatively written in a multiple dependent form from all prior claims that possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the detailed description. Those skilled in the art can recognize other equivalents to the specific embodiments described herein which equivalents are intended to be encompassed by the claims attached hereto.

The invention claimed is:
1. A delivery device comprising:
an inner tube having an inner tube proximal end region and an inner tube distal end region, the inner tube distal end region comprising a first endoprosthesis retaining mechanism;
a middle tube having:
a middle tube distal end region and a middle tube proximal end region and defining a middle tube lumen, the inner tube disposed within the middle tube lumen,
a distal endoprosthesis holder on the middle tube in the middle tube distal end region,
a proximal endoprosthesis holder on the middle tube, the proximal endoprosthesis holder located proximal of the distal endoprosthesis holder,
a distal stopper on the middle tube in the middle tube distal end region, the distal stopper located distal of the distal endoprosthesis holder,
a proximal stopper on the middle tube, the proximal stopper located proximal of the distal stopper and proximal of the proximal endoprosthesis holder, and
an outer surface of the middle tube located proximal of the proximal stopper, the proximal stopper extending radially outward beyond the outer surface of the middle tube-located proximal of the proximal stopper,
wherein the distal endoprosthesis holder and proximal endoprosthesis holder each include a raised portion configured to engage an inner surface of an endoprosthesis; and
an outer tube having an outer tube proximal end region and an outer tube distal end region and defining an outer tube lumen, the middle tube disposed within the outer tube lumen, the outer tube distal end region comprising a second endoprosthesis retaining mechanism;
wherein the inner tube is structured and arranged to displace proximally and distally relative to the middle tube, and
wherein the outer tube is structured and arranged to displace proximally and distally relative to the middle tube.

2. The delivery device of claim 1 wherein the distal end region of the inner tube is distal of the distal end region of the middle tube, and wherein the distal end region of the middle tube is distal of the distal end region of the outer tube.

3. The delivery device of claim 1 further comprising a first handle attached to the proximal end region of the inner tube; a second handle attached to the proximal end region of the middle tube, the second handle distal of the first handle; and a third handle attached to the proximal end region of the outer tube, the third handle distal of the second handle.

4. The delivery device of claim 3 wherein when the delivery device is in an undeployed configuration, a first distance between the first handle and the second handle is in a range of about 0 centimeters to about 2 centimeters.

5. The delivery device of claim 3 wherein a second distance between the second handle and the third handle is in a range of about 0 centimeters to about 2 centimeters.

6. The delivery device of claim 1 further comprising an endoprosthesis that comprises an endoprosthesis distal end constrained on the middle tube by the first endoprosthesis retaining mechanism and an endoprosthesis proximal end constrained on the middle tube by the second endoprosthesis retaining mechanism, wherein the endoprosthesis defines an endoprosthesis lumen, the middle tube disposed within the endoprosthesis lumen.

7. The delivery device of claim 6 wherein the first endoprosthesis retaining mechanism comprises a first sleeve extending proximally over the endoprosthesis distal end.

8. The delivery device of claim 6 wherein the second endoprosthesis retaining mechanism comprises a second sleeve extending distally over the endoprosthesis proximal end.

9. The delivery device of claim 6 wherein the endoprosthesis further comprises an unconstrained medial region extending farther from the middle tube than the constrained endoprosthesis distal end and the constrained endoprosthesis proximal end.

10. The delivery device of claim 6 wherein the endoprosthesis has an endoprosthesis length in a range of about 30 centimeters to about 60 centimeters.

11. The delivery device of claim 6 wherein the endoprosthesis has a low radial force.

12. A device comprising:
an inner member having an inner member proximal end portion and an inner member distal end portion, the inner member distal end portion comprising a first endoprosthesis retainer;
a middle member having a middle member distal end portion and a middle member proximal end portion and defining a middle member lumen, the inner member disposed within the middle member lumen, the middle member having at least one endoprosthesis holder including a raised portion, the middle member further having a distal stopper located distal of the at least one endoprosthesis holder and a proximal stopper located proximal of the at least one endoprosthesis holder, the proximal stopper protruding radially outward beyond an outer surface of the middle member located proximal of the proximal stopper such that the proximal stopper is raised from the outer surface of the middle member;
an outer member having an outer member proximal end portion and an outer member distal end portion and defining an outer member lumen, the middle member disposed within the outer member lumen, the outer member distal end portion comprising a second endoprosthesis retainer; and
an endoprosthesis disposed around the middle member between the proximal and distal stoppers with the raised portion of the at least one endoprosthesis holder engaging an inner surface of the endoprosthesis, wherein a distal end of the endoprosthesis is positioned proximal of the distal stopper and constrained by the first endoprosthesis retainer, and a proximal end of the endoprosthesis is positioned distal of the proximal stopper and constrained by the second endoprosthesis retainer;
wherein the inner member is adapted to slide proximally and distally relative to the middle member, and
wherein the outer member is adapted to slide proximally and distally relative to the middle member.

13. A delivery device comprising:
an inner tube having an inner tube proximal end region and an inner tube distal end region, the inner tube distal end region comprising a first endoprosthesis retaining mechanism;
a middle tube having a middle tube distal end region and a middle tube proximal end region and defining a middle tube lumen, the inner tube disposed within the middle tube lumen, a distal stopper on the middle tube in the middle tube distal end region and a proximal stopper on the middle tube located proximal of the distal stopper, the proximal stopper protruding radially outward beyond an outer surface of the middle tube located proximal of the proximal stopper such that the proximal stopper is raised from the outer surface of the middle tube;
an outer tube having an outer tube proximal end region and an outer tube distal end region and defining an outer tube lumen, the middle tube disposed within the outer tube lumen, the outer tube distal end region comprising a second endoprosthesis retaining mechanism; and
an endoprosthesis disposed around the middle member between the proximal and distal stoppers such that a distal end of the endoprosthesis is positioned proximal of the distal stopper;
wherein the inner tube is structured and arranged to displace proximally and distally relative to the middle tube, and
wherein the outer tube is structured and arranged to displace proximally and distally relative to the middle tube wherein the middle tube further comprising a distal endoprosthesis holder on the middle tube in the middle tube distal end region and a proximal endoprosthesis holder on the middle tube, the proximal endoprosthesis holder located proximal of the distal endoprosthesis holder, the proximal endoprosthesis holder located distal of the proximal stopper and the distal endoprosthesis holder located proximal of the distal stopper, the distal endoprosthesis holder and proximal endoprosthesis holder each including a raised portion configured to engage an inner surface of an endoprosthesis.

14. The delivery device of claim 13, wherein the distal stopper protrudes radially outward from an outer surface of the middle tube.

15. The delivery device of claim 13, wherein the distal end region of the inner tube is distal of the distal end region of the middle tube, and wherein the distal end region of the middle tube is distal of the distal end region of the outer tube.

16. The delivery device of claim 13, further comprising a first handle attached to the proximal end region of the inner tube; a second handle attached to the proximal end region of the middle tube, the second handle distal of the first handle; and a third handle attached to the proximal end region of the outer tube, the third handle distal of the second handle.

* * * * *